United States Patent [19]
Vallana et al.

[11] Patent Number: 5,133,845
[45] Date of Patent: * Jul. 28, 1992

[54] METHOD FOR MAKING PROSTHESIS OF POLYMERIC MATERIAL COATED WITH BIOCOMPATIBLE CARBON

[75] Inventors: Franco Vallana; Pietro Arru, both of Turin, Italy

[73] Assignee: Sorin Biomedica, S.p.A., Saluggia, Italy

[*] Notice: The portion of the term of this patent subsequent to Jan. 28, 2009 has been disclaimed.

[21] Appl. No.: 479,651

[22] Filed: Feb. 14, 1990

Related U.S. Application Data

[60] Division of Ser. No. 462,849, Jan. 3, 1990, which is a continuation of Ser. No. 391,659, Aug. 8, 1989, abandoned, which is a continuation of Ser. No. 11,539, Jan. 6, 1987, abandoned.

[30] Foreign Application Priority Data

Dec. 12, 1986 [IT] Italy ................................ 67924 A/86

[51] Int. Cl.$^5$ ............................................. C23C 14/34
[52] U.S. Cl. ........................... 204/192.15; 204/192.11; 204/192.14; 204/192.16
[58] Field of Search ................... 204/192.11, 192.14, 204/192.15, 192.16, 192.38, 298.04, 298.06, 298.27, 298.28, 298.29

[56] References Cited

U.S. PATENT DOCUMENTS

| | | | |
|---|---|---|---|
| 3,472,751 | 10/1969 | King | 204/192.11 |
| 3,839,182 | 10/1974 | Sager | 204/192.12 X |
| 4,142,958 | 3/1979 | Wei et al. | 204/192.11 |
| 4,448,802 | 5/1984 | Buhl et al. | 204/298.41 X |

FOREIGN PATENT DOCUMENTS 3116040 11/1982 Fed. Rep. of Germany .

OTHER PUBLICATIONS

C. Neissmantel, "Ion Beam ... Structures", J. Vac. Sci. Technol. 18(2), Mar. 1981, pp. 179-185.
B. Banks et al., "Ion Beam ... Films", J. Vac. Sci. Technol. 21(3), Sep./Oct. 1982, pp. 807-814.
Aisenberg et al., "Ion Beam ... Carbon", J. of Appl. Phys., vol. 42, No. 7, Jun. 1971, pp. 2953-2958.

Primary Examiner—Nam Nguyen
Attorney, Agent, or Firm—Shea & Gould

[57] ABSTRACT

A prosthetic device includes a turbostratic biocompatible carbon film firmly adherent to a substrate and having a density of at least 2.1 g/cm$^3$. The carbon preferably is very thin, e.g., less than about one micron. The thin carbon biocompatible film covers at least that portion of the substrate which will be in contact with body tissue and/or fluids to insure against physiological rejection and degradation of the prosthetic device. The carbon can be deposited on a variety of substrates, including low temperature substrates, in situ, without adversely affecting the mechanical properties of the substrate. The prosthetic device of the invention is formed by triode sputtering vacuum deposition at a relatively low temperature to achieve the desired results with respect to the deposited carbon and the substrate and with respect to the required adherence therebetween.

17 Claims, 4 Drawing Sheets

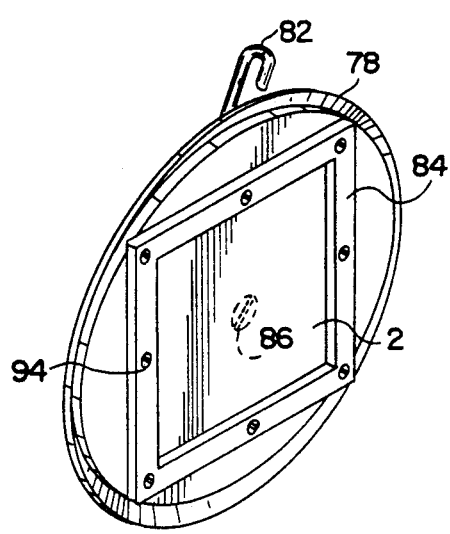
FIG. 2
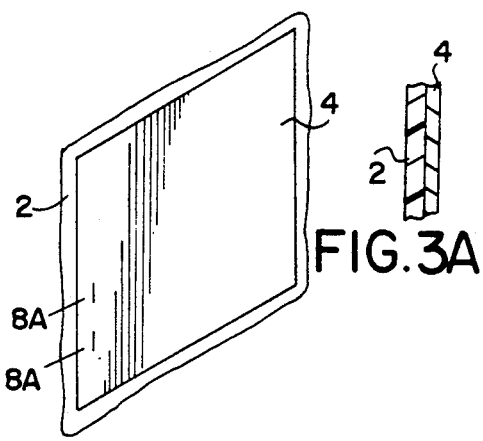
FIG. 3
FIG. 3A
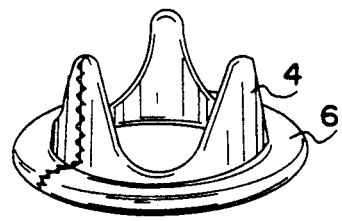
FIG. 4
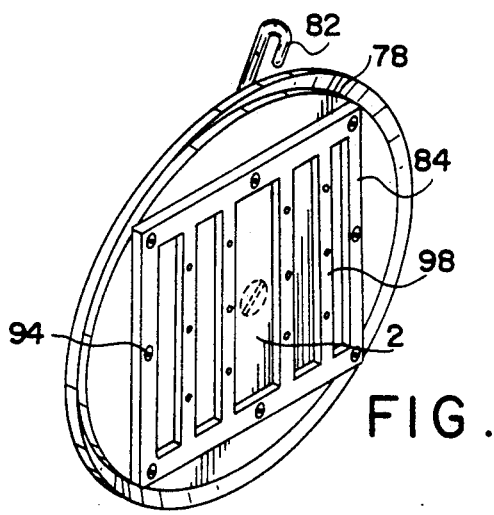
FIG. 5
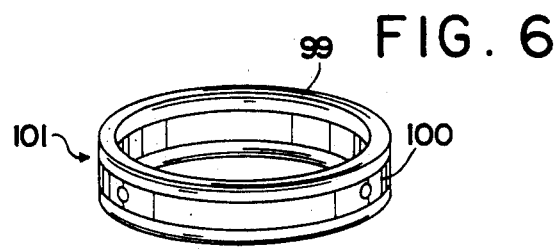
FIG. 6

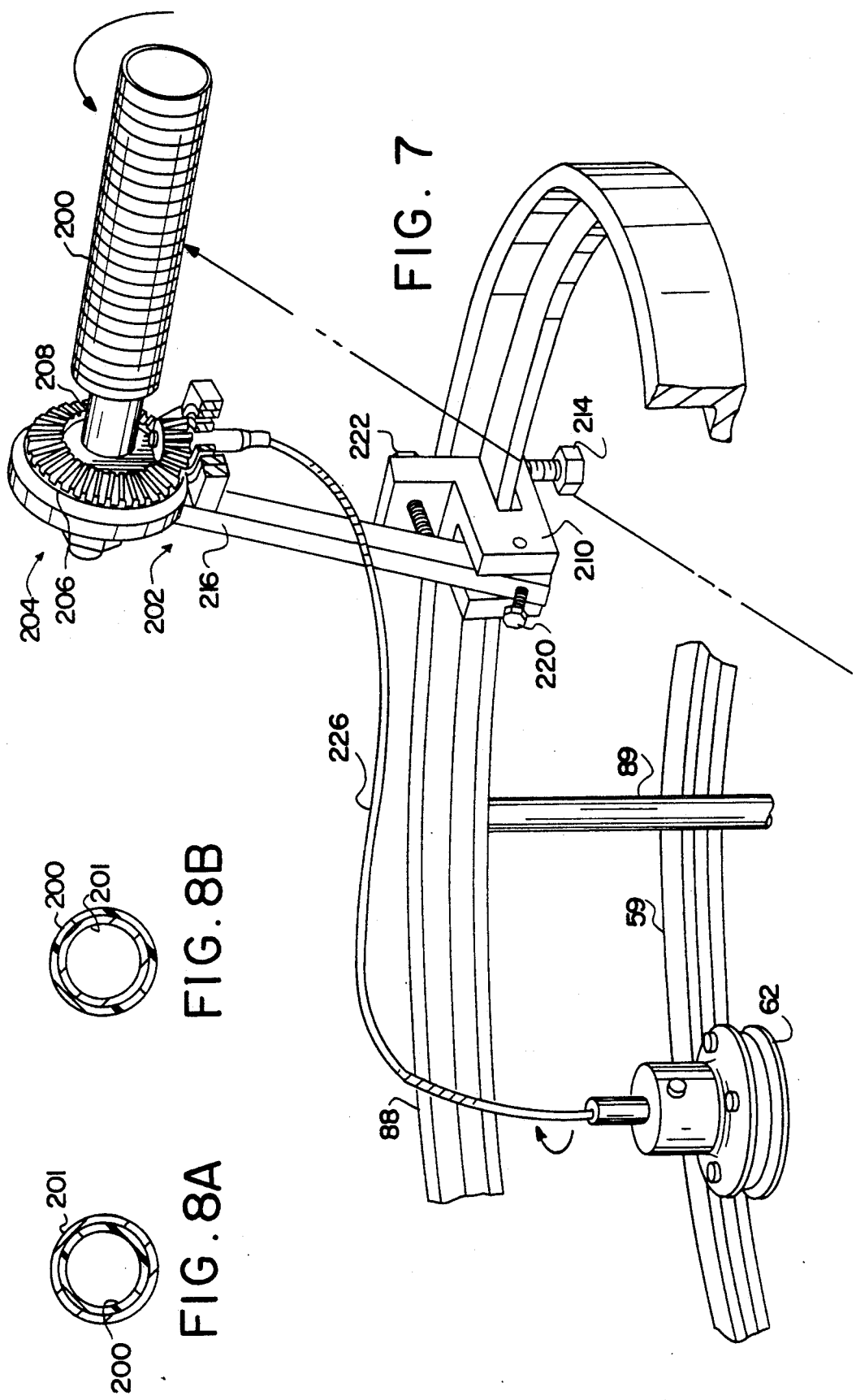

METHOD FOR MAKING PROSTHESIS OF POLYMERIC MATERIAL COATED WITH BIOCOMPATIBLE CARBON

This is a divisional of application Ser. No. 07/462,849 filed Jan. 3, 1990, which is a continuation of Ser. No. 07/391,659 filed Aug. 8, 1989 now abandoned, which is a continuation of Ser. No. 07/011,539 filed Jan. 6, 1987 now abandoned.

FIELD OF THE INVENTION

The present invention is directed to prostheses which can be implanted into the human body and in particular to low temperature substrates which are coated with a high density firmly adherent thin film of biocompatible carbon and to methods of forming such prostheses.

BACKGROUND OF THE INVENTION

In a previous patent application of the Assignee herein, Sorin Biomedica S.p.A. (Italian patent application No. 67978 A/82) filed on Aug. 3, 1982 and corresponding U.S. Ser. No. 801,753, filed Nov. 25, 1986, there is disclosed a triode sputtering method and apparatus which enables the deposition of a biocompatible carbon coating on low temperature substrates (e.g. medical grade Dacron and Teflon) to produce carbon coated prostheses for implanation.

The carbon is described as turbostratic and is preferably deposited in thin layers of less than one micron.

Many fundamental requirements have to be fulfilled by a prosthesis coated with turbostratic carbon, such as, first of all, excellent adhesion of the coating to the prosthesis material (i.e., substrate), a complete and uniform coverage of the substrate, high resistance to wear and obviously, total compatibility of the coated substrate with the organic substances which come into contact with the prosthesis, in particular, blood. Complete and uniform coverage of the prosthesis is obtained by depositing a carbon film with a thickness of not less than about 0.1 micron and utilizing suitable systems for moving the substrate. Resistance to wear is obtained by the physical characteristics of turbostratic carbon and is optimized by means of suitable selection of parameters. Up to the present time, biological compatibility of carbon coatings has been obtained partially by coating with turbostratic carbon obtained by the triode sputtering method mentioned above. In fact, the turbostratic structure of carbon shows the highest biocompatibility that has been obtained up to the present. However, even higher levels of biocompatibility of the coating are still being sought. Research both on the physical characteristics of the coating which could possibly influence biocompatibility and the relevant parameters of the coating procedure and also the reciprocal relationship between parameters have been considered by the applicants herein. In vivo evaluation has been performed in animal tests which have enabled the present inventors to evaluate the biocompatibility of the materials which have been obtained. It has been found that the factor which has the greatest influence on the biocompatibility of the coating is the density of the carbon coating.

It is known in the art to make carbon coated prostheses having a coated density in the range of about 1.5 to 2.0 grams per cubic centimeter. However, the level of biocompatibility of such carbon coated devices has not satisfactorily fulfilled the present requirement of providing prosthetic devices with a high degree of biocompatibility.

Applicants' efforts to increase the density of the carbon coating have been directed to all types of synthetic materials normally in use for prostheses to be implanted into the human body and, in particular, the following materials have been coated: polyurethanes, silicon elastomers, polyesters, polyethylene, polytetrafluoroethylene and polyacetal resins in all possible shapes, in the form of both layers and fibers, yarns and fabric and in more complex shapes. These materials have been coated with turbostratic carbon obtained by the cathode sputtering method described in the previously mentioned Italian patent application No. 67978 A/82 and (U.S. Ser. No. 801,753) incorporated herein by reference) and the parameters of the process (tensions, currents, temperatures, pressures) have been set up according to reciprocal relationships which have been varied in order to obtain the density which was found to yield the desired results. For all such materials the biocompatibility of the coating has been found highly improved with respect to that of coatings obtained using prior methods and lower densities.

Referring to the first requirement mentioned above which is the adhesion of the coating to the substrate, it has been observed that by increasing the density of the carbon coating to improve biocompatibility, the coating is also highly adherent to the substrate.

It is therefore an object of the present invention to provide a method of coating a prosthesis with a thin film of carbon which exhibits an excellent degree of biocompatibility and is firmly adherent to the substrate material.

It is another object of the invention to produce a carbon coating which has a density of at least 2.1 g/cm$^3$ and, preferably at least 2.2 g/cm$^3$.

SUMMARY OF THE INVENTION

The present invention is directed to a method of coating a substrate with a layer of turbostratic carbon having a density of at least 2.1 g/cm$^3$, preferably at least 2.2 g/cm$^3$ and which coating is firmly adherent to the substrate thereby augmenting its biocompatible properties.

The method of the present invention comprises subjecting a source of carbon to a plasma beam generated by triode sputtering under vacuum conditions. Ionization of an inert gas and generation of the plasma beam therefrom is achieved utilizing the apparatus disclosed in previously mentioned U.S. Ser. No. 801,753 incorporated herein by reference. Carbon atoms sputtered off the target are directed to the substrate to thereby deposit a thin biocompatible film on the substrate. The desired density of the carbon deposited on the substrate (2.1 g/cm$^3$, preferably 2.2 g/cm$^3$) is achieved by operating the triode sputtering apparatus under the following conditions:

Filament current 80–90 amps
sputtering voltage 2000–3200 volts
sputtering current 0.1–0.3 amp
pressure $6 \times 10^{-4}$ to $6 \times 10^{-3}$ mbar The highly dense carbon may be deposited on any suitable substrate, regardless of the configuration of the substrate, e.g. flat or curved or undulating. Preferred substrates are low temperature synthetics such as medical grade Dacron and Teflon which may be used to manufacture implantable prostheses such as heart valves, vascular grafts, sutures and the like.

BRIEF DESCRIPTION OF THE DRAWINGS

The following is a detailed description of the method of the invention and products produced thereby. The description is accompanied by drawings of the apparatus used to coat substrates with the improved dense firmly adherent biocompatible layer of carbon.

The coating apparatus is described with particularlity in U.S. Ser. No. 801,753 incorporated herein by reference. Other drawings referred to herein are directed to products made by the process of the present invention.

It is to be understood with respect to the following detailed description that the invention is capable of modification and variation apparent to those skilled in the art within the spirit and scope of the invention.

Figure 1:
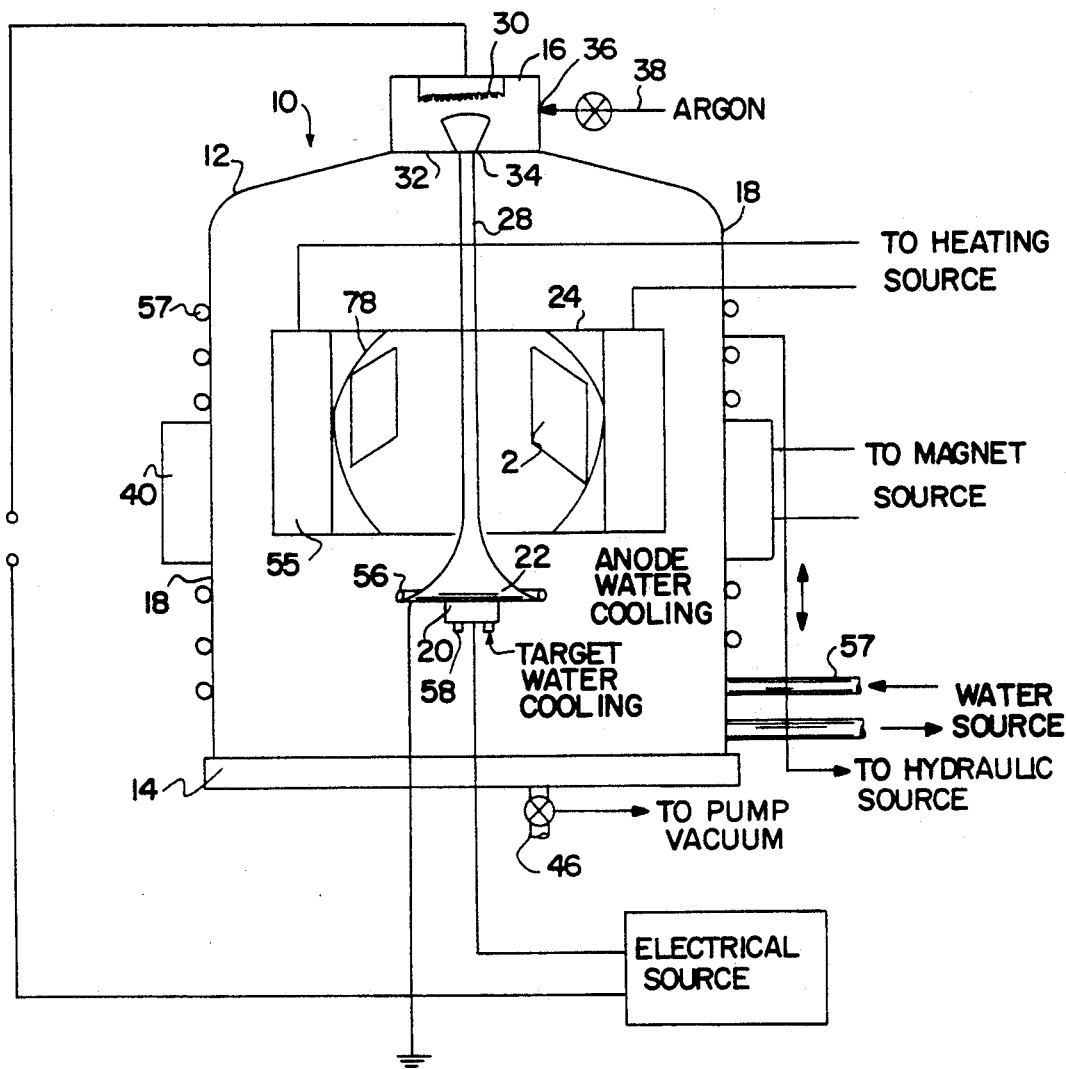

FIG. 1 is a schematic view of the apparatus employed for coating substrates which illustrates the electric circuits, cooling, hydraulic and vacuum systems, along with showing the plasma beam generated in the ionization chamber centered and directed to the target area;

FIG. 2 is a perspective view of a disk and frame for holding a substrate which is to be coated in accordance with the present invention;

FIG. 3 is a perspective view of the coated substrate after it has been removed from the disk and frame shown in FIG. 2.

FIG. 3A is a cross-sectional view of the coated substrate of FIG. 3.

FIG. 4 is a schematic view of a component for a cardiac valve encased within a coated substrate of the present invention;

FIG. 5 is a perspective view of a disk and a frame for holding a substrate which is to be coated in preselected locations in accordance wih the present invention;

FIG. 6 is a perspective view of a ring structure used for a mechanical heart valve with a substrate coated over selected portions.

Figures 9, 10:
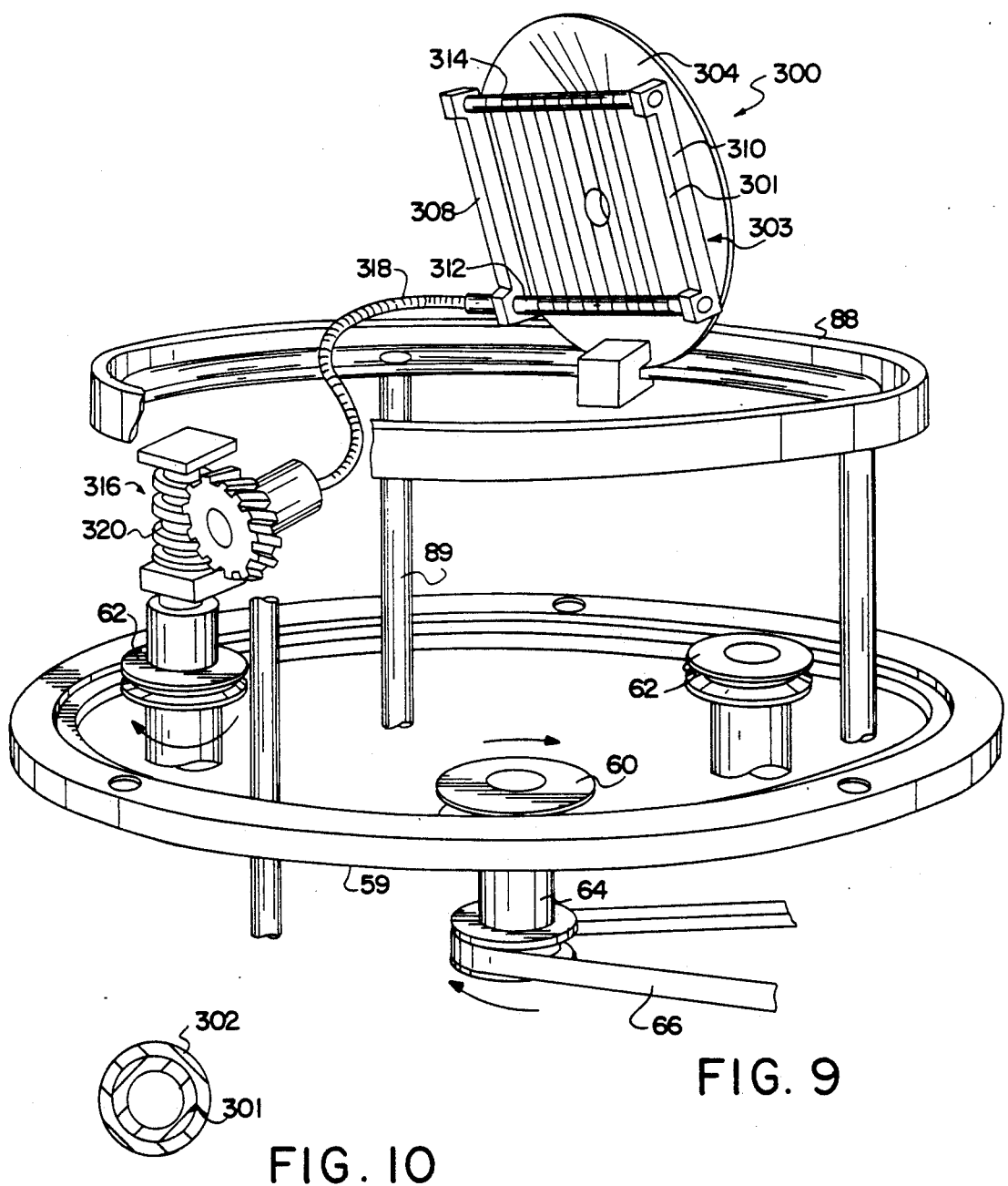

FIG. 7 is a perspective view of an apparatus used for coating tubing, especially for the production of vascular grafts;

FIG. 8A is a cross-sectional view of the coated tubing prior to inversion;

FIG. 8B is a cross-sectional view of the coated tubing after inversion;

FIG. 9 is a perspective view of an apparatus used for coating suture yarn; and

FIG. 10 is a cross-sectional view of the coated yarn.

Referring to FIGS. 1-5, there is shown a triode vacuum apparatus 10 (FIG. 1) for coating a substrate 2 with a thin, uniform, highly dense coating of film 4 of biocompatible carbon firmly adherent to the substrate 2 (FIGS. 3 and 3A) for use in a prosthetic device 6 (FIG. 4).

Details of the structure of apparatus 10 are set forth in U.S. Ser. No. 801,753. Generally, the apparatus 10 includes a bell jar 12 mounted on a base 14. The bell jar 12 has an upper ionization chamber 16 containing a filament 30 and a lower sputtering chamber 18. Positioned in the sputtering chamber 18 is a target 20 which provides a source for the biocompatible carbon and which is circumscribed by an anode 22. Within the sputtering chamber 18 is a removable support structure or housing 24 for the substrates 2 to be coated by the carbon. This illustrative apparatus is of the general type marketed by Balzers AG of Liechtenstein under Model BB 800 033 PE 7503.

The ionization chamber 16 generates a plasma beam 28 of concentrated ionized particles which are drawn to the target 20 for sputtering carbon onto the substrate 2. The chamber 16 includes a filament 30 at its upper end, an auxilliary anode 32 at its lower end having a central opening 34 therethrough and an intermediate inlet 36 for an inert gas, such as argon, which forms the plasma beam 28. The argon gas flows from a source through a valve controlled conduit 38 connected to the inlet 36 and into the ionization chamber 16, wherein the heated filament 30 ionizes the argon into concentrated positively charged ions which are drawn through the opening 34 of the auxilliary anode 32 into sputtering chamber 18 to the target 20. As the argon ions are drawn through the sputtering chamber 18 they are collimated into the shape schematically illustrated in FIG. 1 by a magnetic field coil 40 centrally positioned about the outer wall of the sputtering chamber 18. As desired, gases in the sputtering chamber 18 can be removed by a vacuum pump connected. to a vacuum outlet (not shown) in the base 14 via the valve controlled conduit 46. Throughout the operation the vacuum pump maintains the sputtering chamber 18 at low pressures so that the environmental effect on the force and speed of the sputtered carbon is minimal.

As illustrated in FIG. 1, the target 20 and the substrates 2 are spaced from the ionization chamber. Accordingly the heat generated in forming the plasma beam 28, in substance, does not reach or adversely effect the substrates 2.

The target 20 can comprise graphite, pyrolytic carbon or a combination thereof. The carbon sputtered onto the substrates 2 is in a biocompatible form, namely turbostratic. Under the process conditions of the present invention as described below the carbon deposited on the substrate is firmly adherent thereto and has a density of at least 2.1 g/cm$^3$, preferably at least 2.2 g/cm$^3$ which is important to obtain a highly biocompatible prosthesis.

Applicants have discovered that a highly dense coating of turbostratic carbon may be deposited on a suitable substrate such as Dacron or Teflon in a low temperature process by operating the above-described triode sputtering deposition apparatus at a filament current of 80-90 amps, a sputtering voltage of 2000-3200 volts, a sputtering current of 0..1-0.3 amps and at pressure of $6 \times 10^{-4}$ to $6 \times 10^{-3}$.

More specifically, the filament 30 is operated at 80-90 amps and thereby ionizes argon gas entering the ionization chamber 16 via the intermediate inlet 36.

The charged ions are drawn through the opening 34 of the auxilliary anode 32 and collimated into a beam as shown in FIG. 1 by the magnetic coil 40.

Within the deposition chamber 18, the voltage between the anode 22 and the target cathode 20, referred to herein as the sputtering voltage, is operated in the range of 2000 to 3200 volts and the relevant current at the target 20 is 0.1 to 0.3 amps. The deposition chamber 18 is maintained at a pressure of $6 \times 10^{-4}$ to $6 \times 10^{-3}$ mbar during sputtering.

Referring to FIGS. 2, 3 and 3A a rectangular shaped substrate 2 is secured in a correspondingly shaped frame 84 on a disk 78 by screws or other means 94. After forming the biocompatible carbon film 4 on the substrate 2 in accordance with the present invention, the coated substrate 2 is removed from the frame 84 and can be wrapped around and secured to a stent of a cardiac valve, for example, to form the prosthetic device 6 shown in FIG. 4. In doing so, biocompatible carbon coated sutures, which are preferably also prepared in accordance with the present invention as hereinafter more particularly described, can be used.

Certain prosthetic devices require only portions of the substrate to be coated with a biocompatible carbon film. For example, cardiac valves may have only a portion of the valve exposed to physiological fluids, or it may be desirable to have portions of the prosthetic device attached by tissues after implantation. Those portions not exposed to tissues and fluids or portions which are desirably attached to tissues are masked prior to coating. In such instance the triode sputtering vacuum process of the invention will provide a carbon film only on the unmasked portions. More specifically, and as shown in FIGS. 5 and 6, the frame 84 has masking segments 98 overlaying the substrate 2. As a result, the present invention will provide a substrate 2 including coated and uncoated portions which can be used to form a ring 101 for a cardiac valve comprising a substrate 2 having coated and uncoated regions 99 and 100, respectively.

In addition to the valve components 6 and 101 just described, the present invention can be used for producing grafts and patches, tubular prostheses, sutures, catheters, otologic prostheses, tendon and ligament prostheses, dental implants, jaw replacements and other prosthestic devices. The prosthetic devices of the invention are especially useful as implants because they are biocompatible with body fluids and tissue. The implanted prosthetic devices of the invention resist physiological rejection and degradation. In each embodiment of the invention, the prosthetic device consists of or includes a substrate 2 with a thin, uniform, highly dense film or coating 4 and 99 of biocompatible carbon adherent thereto.

In the present invention, a wide variety of substrate materials can be used, however, the invention is particularly well suited for substrates comprising organic polymers having relatively low softening points. The substrates include DACRON which exhibits a change in elasticity at about 150° C. Therefore, it is preferred when coating DACRON to have the substrate exposed to temperatures no higher than the range of 80°-90° C.

TEFLON is another suitable material which has low softening point substrate. TEFLON can withstand temperatures of about 250° C. before softening. It is preferred to limit the temperature in proximity of a TEFLON substrate to no more than about 160°-180° C.

Other low temperature materials which can be used for the substrate include silicone, polyacetal resins (DELRIN), polyurethane, low density polyethylene, and non-refractory metals, such as Haynes 25 cobalt-chromium alloys, titanium and titanium alloys.

The thickness of the substrates will vary depending on the form of and type of material.

Substrates in the form of woven or knit fabrics, such as DARON or TEFLON fabrics used in cardiac valves typically are from about 0.1 to 1.0 mm in thickness, and desirably 0.3 mm.

As stated, the carbon films or coatings of the invention deposited on the described substrates are biocompatible, continuous, uniform, highly dense and cover at least those portions of the substrates which are in contact with physiological fluids that can degrade uncoated substrates.

The carbon film preferably is thin within the range of from about 0.2 to 0.8 micron. Films having a thickness exceeding the preferred range tend to separate from the substrate and/or take too long to produce. Films below the preferred thickness may not uniformly cover the substrate surface.

The carbon film of the invention is dense, at least 2.1 $g/cm^3$ preferably at least 2.2 $gm/cm^3$, and may typically be in the range of 2.2 to 2.4 $g/cm^3$. The carbon film is turbostratic. In fact this form of carbon is known to be biocompatible. The carbon film of the invention also strongly adheres to the substrate so that the coated substrate is able to repeatedly flex without separation of the film. The adhesion is tested in accordance with the ASTM 03359 standard procedure.

The process of the invention is admirably suited for forming the described biocompatible film on a wide variety of prosthetic devices consisting of or including coated substrates. To highlight the advantages of the invention, the following describes the process utilizing the illustrative embodiment of the apparatus 10 for forming the prosthetic device as shown in FIG. 2 and 3, including a low temperature substrate such as medical grade DACRON.

The substrates 2 to be used are rectangular in shape as shown in FIG. 2. Prior to initiating the operational phase of the process, the DACRON substrates are cleansed by a non-corrosive solvent.

The cleansed substrates 2 are mounted by the frame 84 to the disks 78 (FIG. 2) and the loaded disks 78 are mounted into the deposition chamber 16 using attachment means 82 such as a hook.

The sputtering chamber 18 is then evacuated and maintained at a pressure level of from $6 \times 10^{-3}$–$6 \times 10^{-3}$ mbar and preferably about $4 \times 10^{-3}$ mbar by a vacuum pump via an outlet and conduit 46. This is done to enhance the adhesion of the sputtered and the deposited carbon on the substrates 2.

The target 20 is cleansed by bombardment of the plasma beam 28, and the bell jar 12 is cleansed by removal of moisture and gaseous impurities. The cleansing of the bell jar 12 is accomplished by feeding hot water through the helical conduit 57 about the wall of the sputtering chamber 18 and such chamber 18 is evacuated by a vacuum pump to remove vapors and gases.

Also to enhance adhesion of the sputtered carbon on the substrates 2, the temperature within the sputtering chamber 18 is maintained at about 80° C. by the use of the electric quartz lamps 55.

At the same time the filament 30 is operated at a current of about 80 to about 90 amperes, and preferably about 85 amperes, and argon gas is fed into the chamber 16 via conduit 38 and inlet 36, whereupon a plasma beam 28 is generated consisting of high energy positively charged ions. The plasma beam 28 is drawn from the ionization chamber 16 into the sputtering chamber 18 where it is focused or collimated by the magnetic field coil 40 and directed to the target 20.

The high energy argon ions of the plasma beam 28 bombard the target 20 causing carbon atoms to separate from the surface of the graphite or pyrolytic carbon target and flow in an acute angular direction at substantial speeds onto the substrates 2. The substrates 2 are rotated about the longitudinal axis of the bell jar 12 and about their own axis to enhance uniform deposition of carbon.

During operation, the target 20 is maintained at high voltages and low direct currents, such as 2400 volts and 0.2 amps, by the electric source.

The described process is continued until the carbon film 4 uniformly deposited on the DACRON substrates is about 0.3 microns in thickness. To achieve this thickness, the process is operated for about 6 hours. After the desired thickness of biocompatible carbon film is obtained, the argon gas feed is shut off. After the pressure in the sputtering chamber 18 is raised to atmospheric pressure, the bell jar 12 is opened and the housing 24 is removed from the base 14. Thereafter, the disks 78 are removed from the housing 24 and the coated substrates 2 are removed from the frames 84.

The prosthetic devices thereby obtained include the desired carbon film 4 having a density between 2.2 g/cm$^3$ and 2.4 g/cm$^3$ on the substrate 2 with the necessary adhesion therebetween and without adversely affecting the substrate.

Thus far there has been described, in some detail, the coating of flat substrates 2 for use in prosthetic devices. It is to be understood that the present invention can be used to provide biocompatible carbon films on a variety of prosthetic devices of different configurations, including tubular structures (e.g., vascular tubing and catheters) and yarns (e.g., sutures).

In FIG. 7, for example, vascular tubing 200 is coated with a carbon film 201 of the present invention (FIG. 8A). The illustrative apparatus 202 includes a drive assembly 204 comprising a gear mechanism 206 which rotates a spindle 208 having the tubular substrate 200 thereon. The drive assembly 204 is secured to a stationary rail 88 by a clamp 210 and bolt 214. A bar 216 of the assembly 204 is adjustably secured at one end to the clamp 210 by bolts 220 and 222 and at its other end to the gear mechanism 206.

The gear mechanism 206 is rotated by a rotable flexible cable 226 connected at one end to the gear mechanism 206 and its other end to the previously described idler roller. Rotation of the ring 59 by a driver roller causes the idler roller 62 to rotate cable 226 which, in turn, rotates the gear mechanism 206. In so doing, the gear mechanism 206 rotates the spindle 208 and tubing 200 thereon.

In operation, the tubular substate 200 is rotated during the sputtering process whereby sputtered carbon atoms from the target 20, as already described and illustrated, impinge on the tubular substrate 200 until a uniform thin biocompatible carbon film 201 is obtained. If desired the coated exterior surface of the tubing is turned within itself to provide an inert coated interior surface. Also, this technique can be used for coating both surfaces of the tubing 200 by simply remounting the inverted tubing 200 on the spindle 208 and repeating the process to coat its "new" uncoated exterior surface.

In accordance with the described process tubing of DACRON was coated with the biocompatible carbon film 201 of the invention by rotating the tubing 200 about 5 revolutions per minute in about 9 hours under conditions similar to the described conditions for coating the substrate 2 of DACRON.

Biocompatible carbon coated yarns, such as sutures, also can be produced in accordance with the present invention.

As shown in FIGS. 9 and 10 there is provided a device 300 for coating suture yarn 301 with a uniform, thin highly dense adherent film of biocompatible carbon 302. The device 300, includes a frame 303 attached to a disk 304 secured by a clamp 306 to the stationary rail 88. The frame 303 includes verticle supports 308 and 310 with transverse rods 312 and 314 therebetween.

The lower rod 312 is rotated by a drive assembly 316 including a rotatable flexible cable 318 connected at one end to a gear mechanism 320, which, in turn, is rotatably connected to the previously described idler roller 62. As the lower rotatable ring 59 is rotated by the drive roller 60, such rotation is transferred through the idler roller 62, gear mechanism 320 and flexible cable 318 to the lower rod 312.

The rods 312 and 314 include grooves therein for receiving progressive loops of the suture yarn 301 as it is rotated by the rod 312. As the rod 312 is so rotated, carbon is sputtered from the target 20, and is deposited on and firmly adheres to the moving yarn 301 to form the biocompatible carbon film 302. The grooves are arranged in spaced apart relationship along the rods 312 and 314. As the yarn 301 moves from one groove to another, it is slightly twisted thereby progressively exposing uncoated portions of the yarn to the sputtered carbon.

Following the steps of the described process, suture yarn 301 of DACRON was coated with the biocompatible carbon film 302 of the invention by progressively looping the yarn 301 over the device 300 for about 6.5 hours.

Thus, the present invention includes a wide variety of prosthetic devices, as well as methods of forming a highly dense biocompatible thin film. In its broader aspects, the invention is not limited to the specific described embodiments and departures may be ..made therefrom within the scope of the accompanying claims without departing from the principles of the invention and without sacrificing its chief advantages.

What is claimed is:

1. A method of forming a prosthetic device having a substrate, consisting essentially of:

triode cathodic sputtering of carbon at a low temperature and a pressure of between $6 \times 10^{-4}$ to $6 \times 10^{-3}$ mbar and at a sputtering voltage of from about 2,000 to 3,200 volts and a sputtering current of from about 0.1 to 0.3 amps onto the substrate without degradation thereof to form a continuous turbostratic biocompatible carbon coating having a density of at least about 2.1 g/cm$^3$ on the substrate which is firmly adherent thereto.

2. The method of claim 1, wherein the step of triode cathodic sputtering is conducted at a filament current of rom about 80 to 90 amps.

3. The method of forming a prosthetic deevice according to claim 1, wherein the carbon cathode consists of graphite or pyrolytic carbon or a combination thereof.

4. The method of forming a prosthetic device according to claim 1, wherein the carbon cathode and anode are cooled by water conveyed through conduits continguous therewith.

5. The method according to claim 1, wherein the substrate is flat and is rotated about the carbon cathode and about itself for uniform distribution of the sputtered carbon thereon.

6. The method according to claim 1, wherein the substrate is tubular and is rotated about its axis for uniform distribution of the sputtered carbon thereon.

7. The method according to claim 1, wherein the substrate is suture yarn and is rotated about a frame for uniform distribution of the sputtered carbon thereon.

8. The method according to claim 1, further comprising masking portions of the substrate so that the sputtered carbon only is deposited on unmasked portions.

9. The method according to claim 1, wherein the substrate is a polyester resin and the temperature at the substrate is maintained at about 80° C. to enhance the adhesion of the sputtered carbon to the substrate.

10. The method according to claim 1, wherein the carbon sputtered onto the substrate has a thickness of not more than about 1.0 micron.

11. The method according to cliam 1, wherein the material of the substrate is selected from the group consisting of polyester resins, polytetrafluoroethylene, silicone, polyacetal resins, polyurethanes, polyethylene, cobalt-chromium alloys, titanium and titanium alloys, and wherein the carbon sputtered on the substrate is turbostratic.

12. The method according to claim 1 wherein the substrate is a non-refractory metal.

13. The method according to claim 12 wherein the non-refractory metal is titanium or a titanium alloy.

14. The method of claim 12 wherein the non-refractory metal is a cobalt-chromium alloy.

15. A method of forming a prosthetic device having a substrate, comprising:

forming a plasma beam at a filament current of about 80–90 amps and directing the beam toward a carbon cathode circumscribed by an anode, the cathode and anode being remote from the site of formation of the plasma beam, sputtering the carbon cathode at a pressure of from about $6 \times 10^{-4}$ to $6 \times 10^{-3}$ mbar by said beam while cooling the cathode and anode and operating the cathode at from about 2,000 to 3,200 volts and a current of from about 0.1 to 0.3 amps, and directing said sputtered carbon onto the substrate without degradation thereof to form a biocompatible carbon coating on the substrate which is firmly adherent thereto, and has a density of at least about 2.1 g/cm$^3$.

16. The method of claim 15, wherein the density of the deposited carbon is at least 2.2 g/cm$^3$.

17. The method of claim 16, wherein the density of the deposited carbon is from about 2.2 to 2.4 g/cm$^3$.

* * * * *

UNITED STATES PATENT AND TRADEMARK OFFICE
CERTIFICATE OF CORRECTION

PATENT NO. : 5,133,845
DATED : July 28, 1992
INVENTOR(S) : FRANCO VALLANA and PIETRO ARRU It is certified that error appears in the above-identified patent and that said Letters Patent is hereby corrected as shown below:

On the title page, item [60] "Related U.S. Application Data"

The Division Application Serial No. is --464,629-- and not "462,849".

The Continuation Application Serial No. 07/011,539 was filed on --February 6, 1987-- and not "January 6, 1987".

Signed and Sealed this

Sixteenth Day of November, 1993

Attest:

BRUCE LEHMAN

*Attesting Officer*  *Commissioner of Patents and Trademarks*